(12) United States Patent
Curti et al.

(10) Patent No.: US 7,364,682 B2
(45) Date of Patent: *Apr. 29, 2008

(54) NASAL AND ORAL CANNULA BREATHING DETECTION DEVICE

(75) Inventors: James N. Curti, Backersfield, CA (US); Peter W. Salter, Tehachapi, CA (US)

(73) Assignee: Salter Labs, Arvin, CA (US)

( * ) Notice: Subject to any disclaimer, the term of this patent is extended or adjusted under 35 U.S.C. 154(b) by 472 days.

This patent is subject to a terminal disclaimer.

(21) Appl. No.: 10/730,291

(22) Filed: Dec. 5, 2003

(65) Prior Publication Data

US 2004/0112383 A1    Jun. 17, 2004

Related U.S. Application Data (60) Continuation-in-part of application No. 10/265,527, filed on Oct. 4, 2002, now Pat. No. 6,830,445, which is a division of application No. 09/883,843, filed on Jun. 18, 2001, now Pat. No. 6,533,984, which is a continuation-in-part of application No. 09/754,471, filed on Jan. 4, 2001, now Pat. No. 6,533,983.

(51) Int. Cl.
*B29C 33/40* (2006.01)
*B29C 33/42* (2006.01)
*B29C 33/60* (2006.01)
*B29C 41/14* (2006.01)

(52) U.S. Cl. ............ 264/219; 264/304; 264/305; 264/327; 264/337; 264/338

(58) Field of Classification Search ........ 264/219, 264/221, 304, 305, 327, 337, 338; 425/275; 128/204.18, 207.14, 207.18
See application file for complete search history.

(56) References Cited

U.S. PATENT DOCUMENTS

| 2,053,357 | A | 9/1936 | Winder ............... 18/41 |
| 2,296,011 | A | 9/1942 | Beal |
| 2,824,407 | A | 2/1958 | Ebel |
| 2,854,695 | A | 10/1958 | Moreau |
| 3,643,660 | A | 2/1972 | Hudson et al. ........ 128/206 |
| 3,731,900 | A | 5/1973 | Havstad ............ 249/177 |
| 3,802,431 | A | 4/1974 | Farr ............. 128/207.18 |

(Continued)

FOREIGN PATENT DOCUMENTS

EP    0 993 094 A2    4/2000

(Continued)

OTHER PUBLICATIONS

Salter Labs, "Dual Oral/Nasal ETCO 2 Sampling Cannulas", Copyright 1991, Revised Sep. 2003.

*Primary Examiner*—Leo B. Tentoni
(74) *Attorney, Agent, or Firm*—Davis Bujold & Daniels PLLC (57) ABSTRACT

A cannula and method of forming a cannula by forming a cannula mandrel assembly having a nare mandrel, a main body mandrel and mouthpiece mandrel; heating the cannula mandrel assembly, applying a polymeric material to the cannula mandrel assembly to provide a desired material thickness on the mandrel assembly to form the cannula, curing the polymeric material of the formed cannula and extracting the mandrel assembly from the cannula by disassembly and removal of the mandrel assembly parts.

20 Claims, 10 Drawing Sheets

U.S. PATENT DOCUMENTS

| | | | |
|---|---|---|---|
| 3,906,071 A | 9/1975 | Cook et al. | 264/255 |
| 3,931,381 A | 1/1976 | Lindberg | 264/45.5 |
| 4,106,505 A | 8/1978 | Salter et al. | 128/206 |
| 4,152,688 A | 5/1979 | Dietz | 338/215 |
| 4,433,219 A | 2/1984 | Dietz | 200/83 R |
| 4,602,643 A | 7/1986 | Dietz | 128/721 |
| 4,695,241 A | 9/1987 | Ventimiglia | 425/275 |
| 4,745,925 A | 5/1988 | Dietz | 128/725 |
| 4,800,116 A | 1/1989 | Ventimiglia et al. | 428/215 |
| 4,818,320 A | 4/1989 | Weichselbaum | 156/227 |
| 4,878,502 A | 11/1989 | Dietz | 128/725 |
| 5,005,571 A | 4/1991 | Dietz | 128/205.25 |
| 5,024,219 A | 6/1991 | Dietz | 128/204.21 |
| 5,038,771 A | 8/1991 | Dietz | 128/204.21 |
| 5,046,491 A | 9/1991 | Derrick | 128/200.24 |
| 5,052,400 A | 10/1991 | Dietz | 128/722 |
| 5,074,299 A | 12/1991 | Dietz | 128/204.21 |
| 5,133,923 A | 7/1992 | Klug | |
| 5,335,656 A | 8/1994 | Bowe et al. | 128/207.18 |
| 5,380,182 A | 1/1995 | Packard et al. | 425/275 |
| 5,485,833 A | 1/1996 | Dietz | 128/204.23 |
| 5,485,850 A | 1/1996 | Dietz | 128/716 |
| 5,513,634 A | 5/1996 | Jackson | 128/207.18 |
| 5,682,881 A | 11/1997 | Winthrop et al. | 128/207.18 |
| 5,922,365 A | 7/1999 | Reichner | |
| 6,045,514 A | 4/2000 | Raviv et al. | |
| 6,171,258 B1 | 1/2001 | Karakasoglu et al. | |
| 6,213,955 B1 | 4/2001 | Karakasoglu et al. | |
| 6,217,818 B1 | 4/2001 | Collette et al. | 264/513 |
| 6,247,470 B1 | 6/2001 | Ketchedjian | 128/200.28 |
| 6,379,312 B2 | 4/2002 | O'Toole | 600/529 |
| 6,635,214 B2 | 10/2003 | Rapacki | |
| 2002/0171175 A1 | 11/2002 | Ainsworth et al. | |
| 2005/0051176 A1 | 3/2005 | Riggins | |

FOREIGN PATENT DOCUMENTS

| | | |
|---|---|---|
| RU | 1775957 C | 9/1995 |
| RU | 1793628 C | 10/1995 |

NASAL AND ORAL CANNULA BREATHING DETECTION DEVICE

This application is a continuation in part application of U.S. application Ser. No. 10/265,527 filed Oct. 4, 2002 now U.S. Pat. No. 6,830,445, which is a divisional of U.S. application Ser. No. 09/883,843 filed Jun. 18, 2001 now U.S. Pat. No. 6,533,984, which is a continuation in part of U.S. application Ser. No. 09/754,471 filed on Jan. 4, 2001 which is now U.S. Pat. No. 6,533,983 dated Mar. 18, 2003.

This invention provides a novel cannula and a method of producing cannulas suitable for use in both nasal and oral applications, using disconnectable mandrel parts to form the mold over which cannula forming plastics material is applied to form the cannula.

BACKGROUND OF THE INVENTION

This invention relates generally to cannulas adapted for both mouth and nasal use to both monitor breathing and deliver a gas, in particular, a method of manufacturing a cannula adapted to interconnect with both nasal passages and the mouth for use to monitor breathing, especially for the detection of apnea.

Nasal cannulas are commonly used to administer gases, such as oxygen, to humans having respiratory problems. Illustrations of nasal cannulas used for this purpose are found in U.S. Pat. No. 3,802,431. Nasal cannulas have been used also for inhalation therapy, made possible by development of inhalation sensors such as described in U.S. Pat. No. 4,745,925. A nasal cannula can be used to monitor breathing and for detection of apnea (the absence of breathing) when connected to an inhalation sensor.

Nasal cannulas additionally adapted to communicate with the mouth of humans to permit administration of fluids or sensing of apnea during periods of mouth breathing or nasal blockage are also known.

The present invention is a novel cannula and method of manufacturing a cannula to communicate with both nasal and oral passages. This method provides in the preferred embodiment, disconnectable mandrels, which when assembled form a mold over which a cannula forming polymeric material is applied, and which, through the capability of being disconnected, each mandrel part from the other(s), facilitates removal of the mandrels from the formed cannula.

The prior art of dipping a part in a plastisol to create a coating thereof is exemplified by U.S. Pat. Nos. 3,906,071, 4,695,241 and 4,800,116, the disclosures of which are hereby incorporated by reference.

SUMMARY OF THE INVENTION

It is an object of the invention to provide a method of manufacturing cannulas using an assembly of disconnectable mandrels over which cannula forming polymeric material is applied. Application of the plastics material over the mandrel assembly and subsequent extraction of the mandrel sections following curing of the cannula material provides a finished cannula with contiguous internal flow paths to monitor a patent's breathing.

It is a further object of the invention to provide a multi-part mandrel assembly for forming a cannula which facilitates extraction of the mandrel assembly sections after at least partial curing the polymeric material forming the cannula.

Still another object of the invention is to form the main body forming mandrel as two separate, slightly spaced apart components which remain spaced apart from one another by a void, during the dipping process, so that the void becomes filled with a plastisol to form a septum or barrier which divides the internal passage into two compartments or passageways, one which facilitates the supply of supplemental oxygen to a patient while the other facilitates monitoring of the breathing of the patient.

Another object of the invention is to produce a cannula having a mouthpiece extending from the main body of the cannula to the patients mouth, the cannula is provided with a passageway for supplying a gas to the patient via a demand regulator for example, or sampling a patients oral exhalations for determining a blood level carbon dioxide level for instance, and providing the mouthpiece with a retainer passage for holding a dead soft material enabling the mouthpiece to be bent, shaped or molded into a desired curvature for positioning the opening of the mouthpiece in the patient's oral exhalation path.

According to the invention, there is provided a method of forming a cannula comprising separable parts including the steps of providing a cannula mandrel assembly, said assembly comprising at least one nare forming mandrel, at least one mouthpiece forming mandrel, and a main body forming mandrel; heating the cannula mandrel assembly to a desired temperature; providing an uncured cannula forming polymeric material in flowable state; applying at least one coating of the material to the cannula mandrel assembly to provide a desired coating material thickness on the cannula mandrel assembly to form the cannula; at least partially curing the material coating the cannula mandrel assembly; and disassembling the cannula mandrel assembly and withdrawing the at least one nare forming mandrel, and the at least one mouthpiece forming mandrel and the main body forming mandrel from the cannula.

Also according to the invention there is provided a method of forming a cannula comprising the steps of providing cannula mandrel assembly parts, said parts comprising a pair of nare forming mandrels, a main body forming mandrel having a central rectangular recessed section and openings to receive and engage ends of the nare forming mandrels, and a mouthpiece forming mandrel having an end connector, the end connector defining a slot dimensioned to mate slidingly with the rectangular recessed section; assembling the parts to provide a cannula mandrel assembly defining interior spaces of the cannula; heating the cannula mandrel assembly to a desired temperature; providing a cannula forming polymeric material as a plastisol; dipping the heated cannula mandrel assembly in the plastisol to provide a desired thickness of partially cured polymer on the cannula mandrel assembly to form the cannula; heating the cannula material of the cannula to further cure the cannula material; and extracting the nare forming mandrels, the mouthpiece forming mandrel by removing the slot from the rectangular recess, and the main body forming mandrel from the cannula.

Also according to the invention there is provided a method of forming a cannula comprising the steps of a) providing parts for a cannula mandrel assembly comprising a nare forming mandrel, a main body forming mandrel and a mouthpiece forming mandrel having an end connector to slidably engage the main body forming mandrel; b) removably mounting the nare forming mandrel to the main body forming mandrel to provide a desired orientation of the nare forming mandrel relative to the main body forming mandrel and slidably engaging the connector with the main body forming mandrel to provide a desired orientation of the mouthpiece forming mandrel relative to the nare forming mandrel and the main body forming mandrel to form the cannula mandrel assembly; c) heating the cannula mandrel assembly to a desired temperature; d) dipping the heated cannula mandrel assembly into a plastisol of a polymeric material to provide a desired thickness of polymeric material on the cannula mandrel assembly to form the cannula; e) at least partially curing the polymeric material; f) extracting the nare forming mandrel, the mouthpiece forming mandrel, and the main body forming mandrel from the cannula by reversing the assembly steps of subparagraph b).

Also according to the invention there is provided a cannula mandrel assembly, defining the interior cavity of a cannula having a main body, a nare and a mouthpiece, comprising an elongate nare forming mandrel; an elongate mouthpiece forming mandrel; and an elongate main body forming mandrel defining a recessed rectangular section slidably receiving, engaging and supporting a connector end feature of the mouthpiece forming mandrel and defining a transverse opening receiving, engaging and supporting an end of the nare forming mandrel.

BRIEF DESCRIPTION OF THE DRAWINGS

The invention will now be described, by way of example, with reference to the accompanying drawings, in which.

DETAILED DESCRIPTION OF THE EMBODIMENTS

Figure 1:
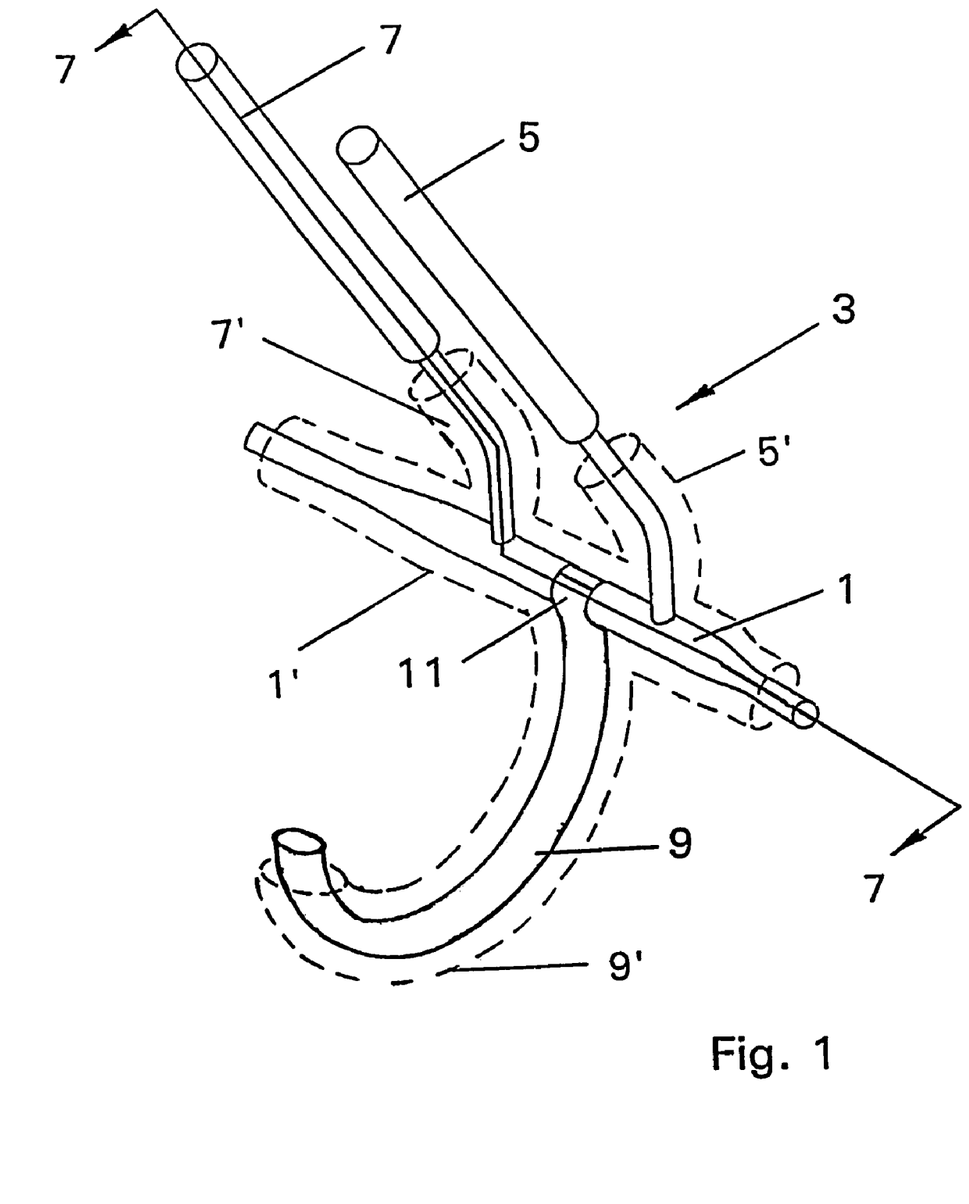
FIG. 1 is an orthogonal view of a cannula mandrel assembly with cannula forming polymeric material shown in ghost.

Referring to FIG. 1, the main body forming mandrel 1 of a beryllium copper cannula mandrel assembly 3 is shown with nare forming mandrels 5 and 7, and a mouthpiece forming mandrel 9 with end connector 11, for joining the mouthpiece mandrel 9 to the main body forming mandrel 1. Shown in ghost is a cannula formed on the assembly and comprising a main body 1', a pair of nares 5', 7' and a mouthpiece 9' composed of polyvinyl chloride (PVC).

Figure 2:
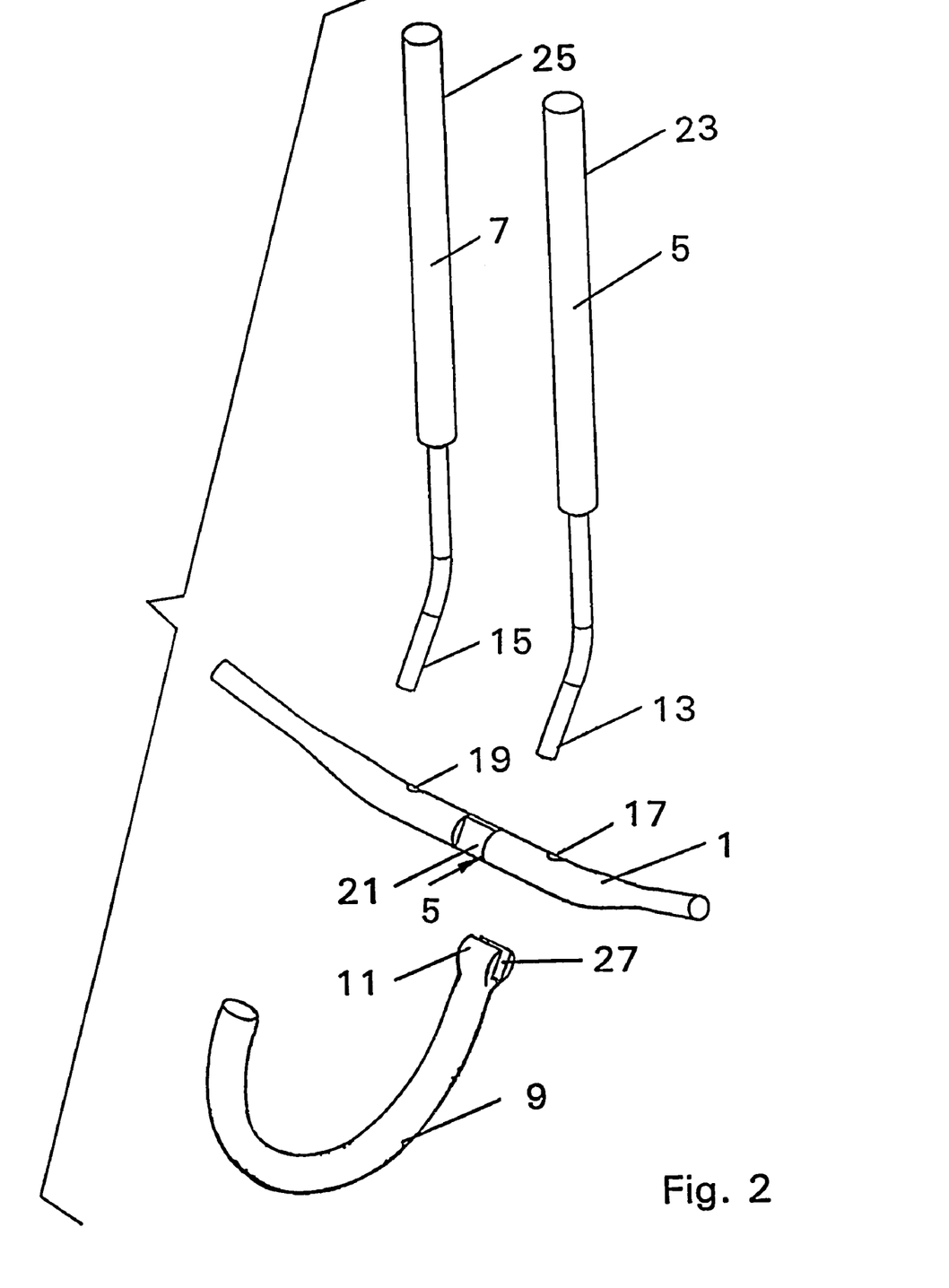
FIG. 2 is an orthogonal view of the cannula mandrel parts prior to assembly.

FIG. 2 shows the mandrel assembly parts prior to assembly to produce the cannula mandrel assembly 3. Nare mandrels 5 and 7 have reduced diameter sections 13 and 15 to form nares 5', 7', respectively, over which cannula material is applied. Reduced diameter sections 13 and 15 of nare mandrels 5 and 7 mate slidably with blind holes 17 and 19 of main body mandrel 1. Main body mandrel 1 also has a rectangular recessed section 21 to slidably mate with end connector 11 of mouthpiece mandrel 9.

Nare mandrels 5 and 7 also have enlarged diameter sections 23 and 25 to support the mandrel in a jig. Additionally, the enlarged diameter enables sections 23 and 25 to provide a larger contact surface to provide grip for removal of nare mandrels 5 and 7 from main body mandrel 1 after partial curing of the PVC on mandrel assembly 3.

FIG. 2 further shows the mouthpiece mandrel 9 with the end connector 11 which has a slot 27 to slidably engage the rectangular section 21 of the main body mandrel 1. Slot 27 is sized to permit close contact of slot 27 with the rectangular section 21 of main body mandrel 1 such that a snug fit is obtained to removably retain the mouthpiece mandrel 9 on the main body mandrel 1 while facilitating extraction from rectangular section 21 following partial curing and cooling of the PVC. The outer surface of end connector 11 approximates the outer diameter of main body mandrel 1 to provide a uniform diameter of applied cannula material and to facilitate withdrawal of the mouthpiece mandrel 9 from the mouthpiece 9' of the cannula.

Figure 3:
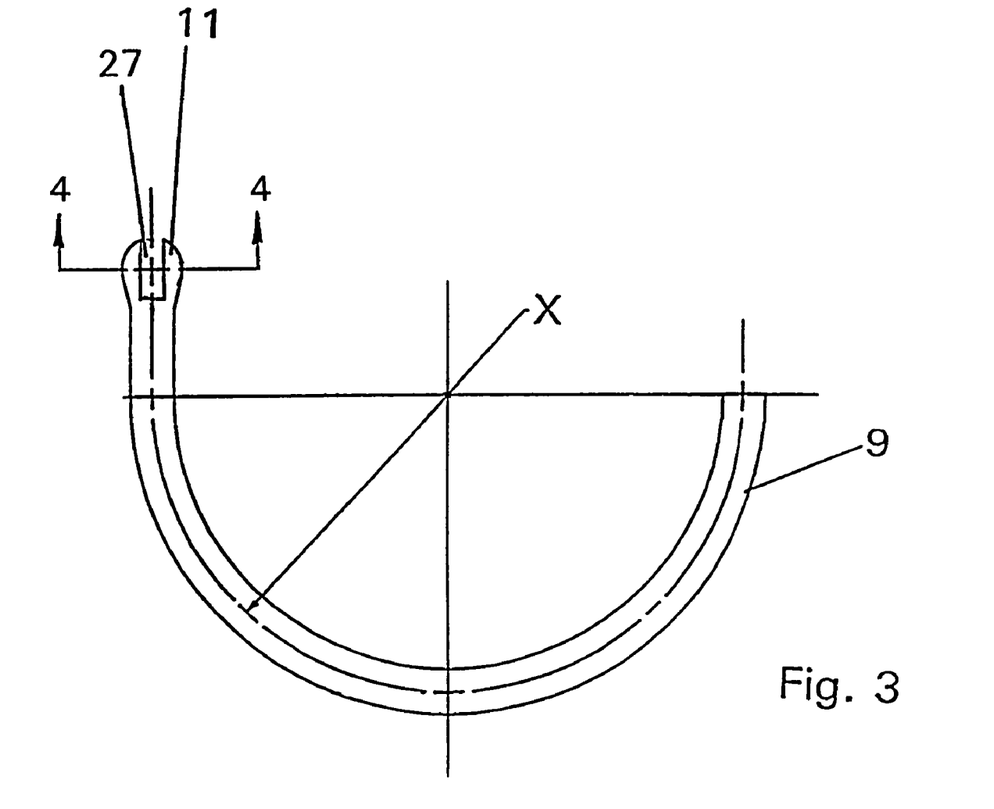
FIG. 3 is a side elevation of the mouthpiece mandrel of FIGS. 1 and 2 showing an end connector.

FIG. 3 shows mouthpiece mandrel 9 having a desired radius X and end connector 11 with slot 27.

Figure 4:
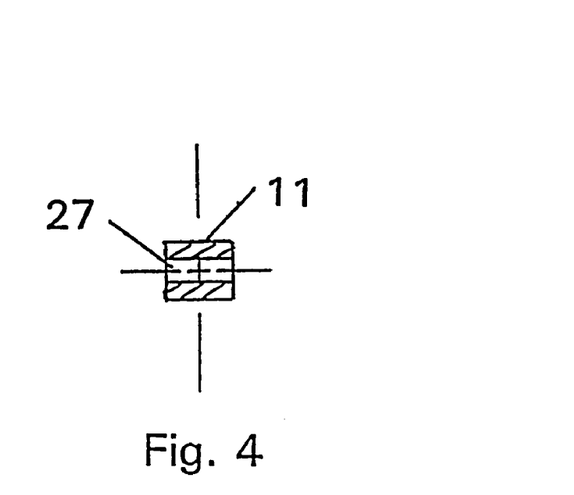
FIG. 4 is an end section of the end connector taken on section 4-4 of FIG. 3.

FIG. 4 shows the shape of end connector 11 and slot 27 through section 4-4 of FIG. 3.

Figure 5:
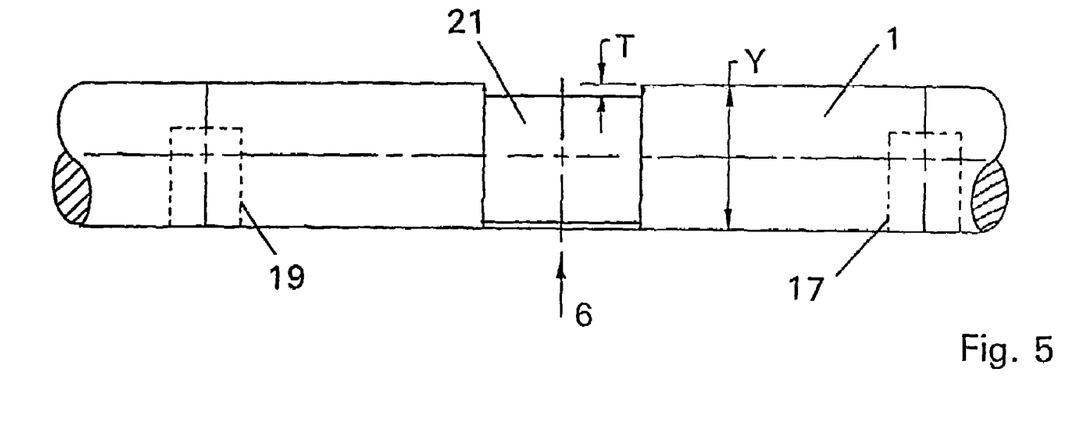
FIG. 5 is a fragmentary side elevation of the main body mandrel of FIGS. 1 and 2 taken in the direction of arrow 5 in FIG. 2.
Figure 6:
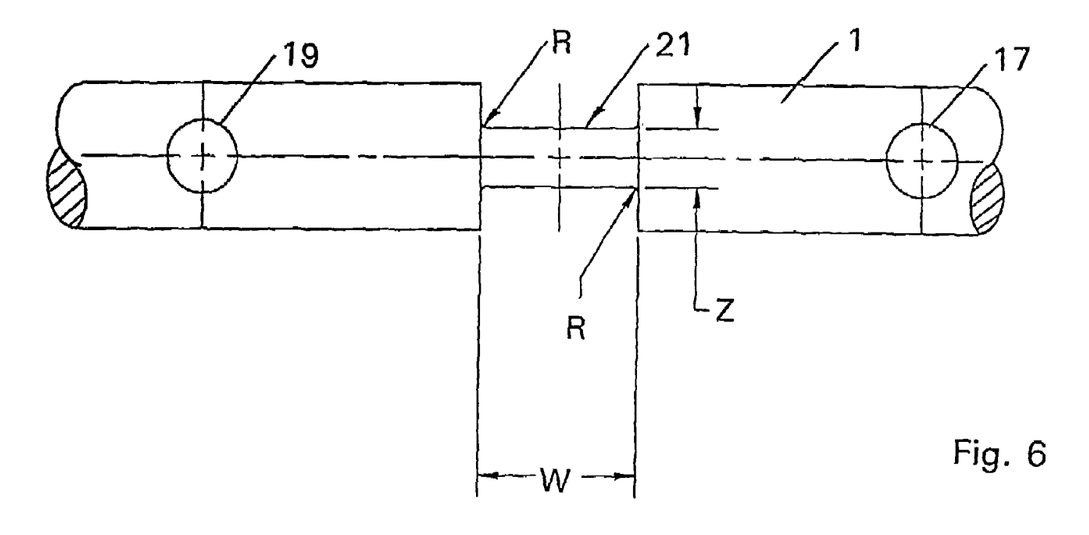
FIG. 6 is an elevation of the main body mandrel taken in the direction of arrow 6 in FIG. 5.

Referring to FIGS. 5 and 6, blind holes 17 and 19 are sized to mate slidably with reduced diameter sections 13 and 15 of the nare mandrels 5 and 7 in order to engage and support nare mandrels 5 and 7 during application of the PVC to form the cannula on the assembly 3. The rectangular section 21 is made with shoulder depth T removed to allow the diameter of end connector 11 of mouthpiece mandrel 9 to mate approximately flush with the diameter Y of main body 1.

Rectangular section 21 is shown with preferred relieving radii R at opposed ends of the section. Radius R may be omitted if main body mandrel 1 is machined or formed in a manner that allows this. Thickness Z of rectangular section 21 permits slot 27 of end connector 11 of mouthpiece mandrel 9 to firmly but slidably mate with rectangular section 21. Width W of rectangular section 21 is just sufficient to closely accommodate end connector 11 of mouthpiece mandrel 9.

FIGS. 1 and 2 show nare mandrels 5 and 7 with bend sections. These bend sections direct the nares of the cannula into a patient's nasal cavities.

Although beryllium copper is the preferred material for the cannula mandrel assembly 3, other materials which possess appropriate working temperature ranges, retain dimensional stability for reuse in a manufacturing environment and which will release the cannula easily after curing of the PVC may be used. Metals including but not limited to the steels, aluminum, bronze, brass, and copper alloys may be used, as well as some plastics. Beryllium copper is preferred due to its ability to transfer heat rapidly and reliably release the cured plastics material of the cannula formed thereon. Rapid heat transfer is desirable for the mandrel material, both during heating cannula mandrel assembly 3 and following cannula material application, when a partial cure of the material is followed by rapid cooling.

Prior to application of a latex solution of PVC (plastisol) the cannula mandrel 3 is coated, usually by dipping, with a silicone release layer to facilitate removal of the mandrel from the plastisol to be applied. The application of the PVC in the preferred embodiment is by dipping the silicone coated cannula mandrel assembly 3 which has been heated in an oven at an oven temperature of from about 350° F. to about 550° F. (preferably about 450° F.) for about 1 to about 3 minutes into a latex solution of PVC (plastisol). One or more dipping steps may be performed to achieve the desired finished cannula material thickness and each of these dipping steps may be for 10-30 seconds. During dipping the mandrel is supported by the outer end portions of the nare mandrels.

The preferred use of a latex solution of PVC (plastisol) provides a semi-clear finished cannula with strength to withstand attachment of connectors and flexibility to prevent injury to the user. Alternatively, other plastics materials, which provide material properties suitable for this method, capable of forming a plastisol may be substituted for PVC.

Partial curing of the cannula takes place on the mandrel assembly 3. The cannula mandrel assembly with the partially cured PVC thereon is then placed in an oven a sufficient time for further curing at a temperature from about 410° F. to about 450° F. Following curing to stabilize the PVC and after the cannula has cooled sufficiently to allow mandrel removal with the assistance of the release layer, without damaging the cannula, while providing sufficient physical strength to retain cannula shape, the mandrel parts are removed from the cannula.

Using the inventive method, a cannula with two nares and a mouthpiece is formed as follows: a cannula mandrel assembly 3 is formed by first, slidably mating reduced diameter sections 13 and 15 of nare mandrels 5 and 7 with blind holes 17 and 19, respectively, of the main body mandrel 1; second, orienting nare mandrels 5 and 7; third, slidably mating slot 27 of end connector 11 of the mouthpiece mandrel 9 with the rectangular section 21 of main body mandrel 1 in a desired orientation relative to nare mandrels 5 and 7; fourth, providing a silicone release layer substantially encompassing the mandrel; fifth, heating the assembled cannula mandrel assembly in an oven at a temperature of from about 350° F. to about 550° F.; sixth, providing a liquid uncured latex PVC mix (plastisol); seventh, dipping the cannula mandrel assembly into the plastisol, at least once, until the desired material thickness on the assembly is achieved; eighth, at least partially curing the PVC at a temperature of about 410° F. to from about 450° F.; and ninth, removing the nare mandrels 5 and 7 from the blind holes 17 and 19 of main body mandrel 1 and the nares 5', 7' by pulling on enlarged diameter sections of nare mandrels 5 and 7, removing mouthpiece mandrel 9 from the mouthpiece 9' by disconnecting slot 27 of end connector 11 from rectangular section 21 of main body mandrel 1 and pulling the mouthpiece mandrel 9 through the mouthpiece 9'; and finally slidably removing main body mandrel 1 from the main body 1' of the cannula.

Figure 7:
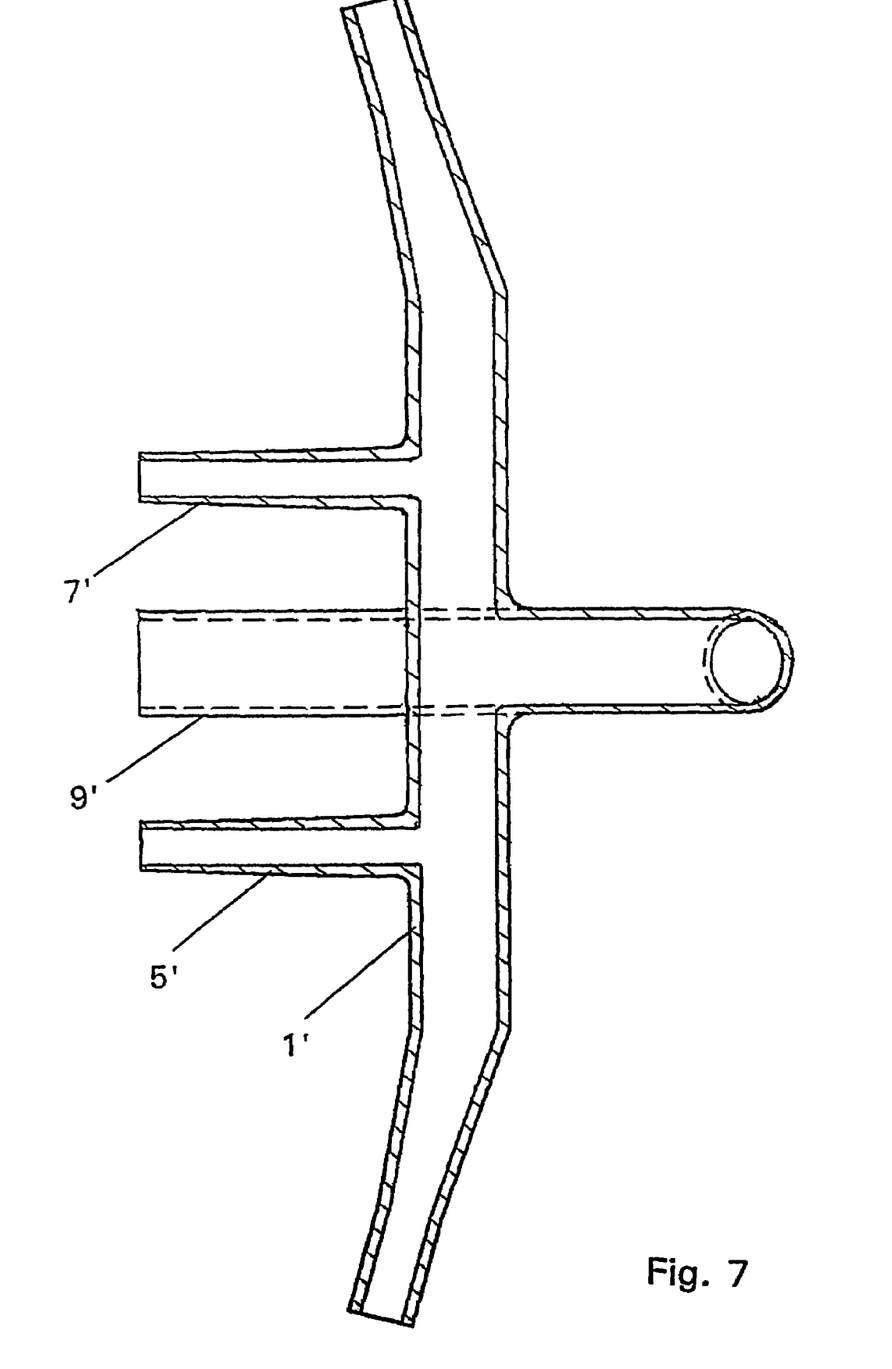
FIG. 7 is a general cross-section of a cannula made by the method of the present invention taken in the direction of section 7-7 of FIG. 1.
Figure 8:
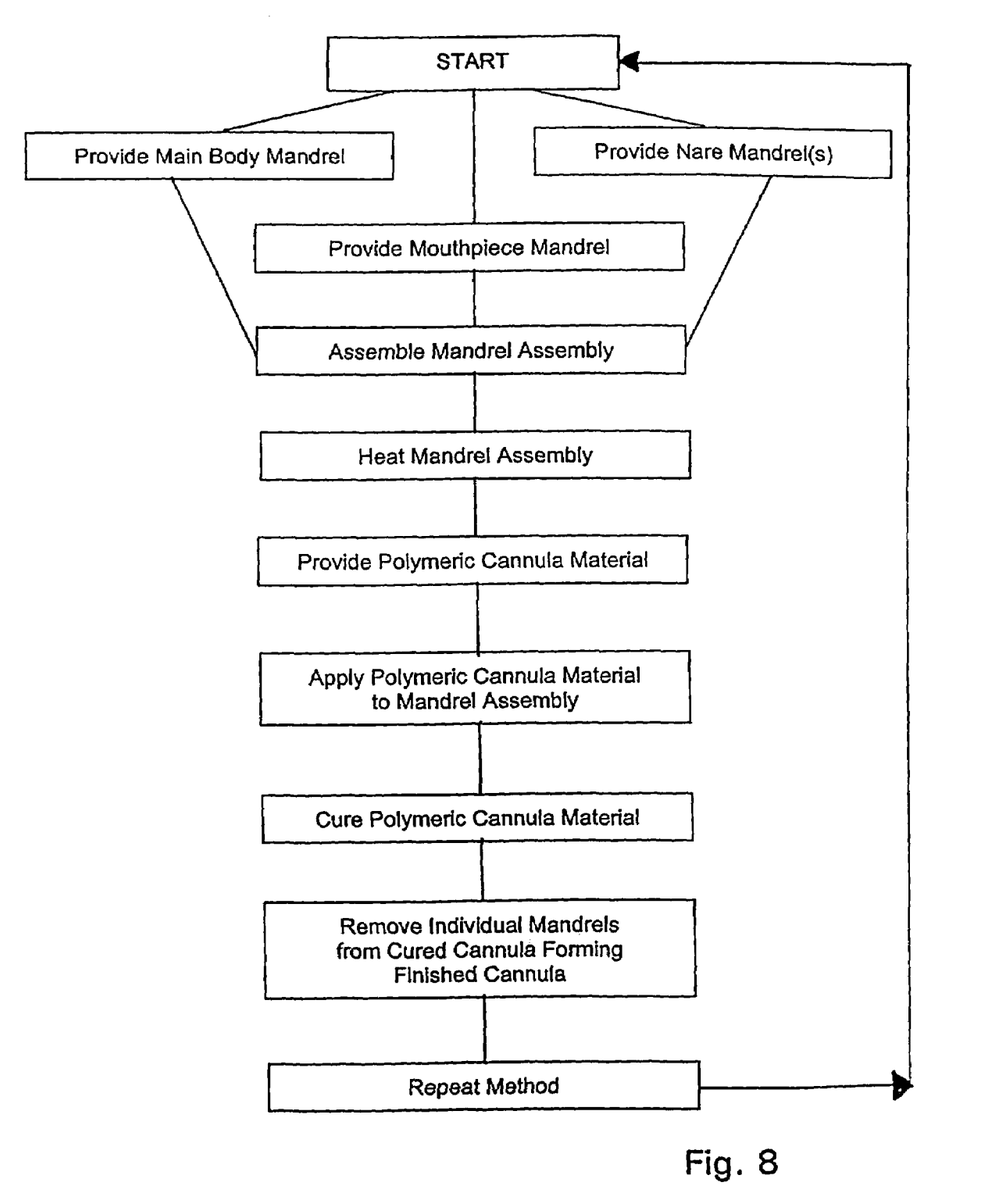
FIG. 8 is a flow diagram of the method of the present invention.

FIG. 7 show a finished cannula, following removal of cannula mandrel assembly 3 parts from the cured PVC, showing contiguous flow paths through the main body 1', nares 5' and 7' and mouthpiece 9'.

It will be appreciated that the curing step may be completed in two stages, a first partial cure of the PVC produced by the heated cannula mandrel assembly 3 sufficient to maintain the PVC on this assembly and a second step in an oven at the above curing temperatures to complete the curing of the PVC.

It will be further appreciated that the outer ends of the main body 1' may be trimmed to provide a discrete area where connecting tubing may be connected thereto, e.g. by solvent bonding, and that the mouthpiece may be trimmed to a length suited to an individual patient so as to maximize the sensitivity of the finished device.

It will also be understood that disassembly of the cannula mandrel assembly, following cannula material cure, can proceed by removing the mouthpiece mandrel before the nare mandrels as obvious alternative method steps, prior to removal of the main body mandrel.

Figure 9:
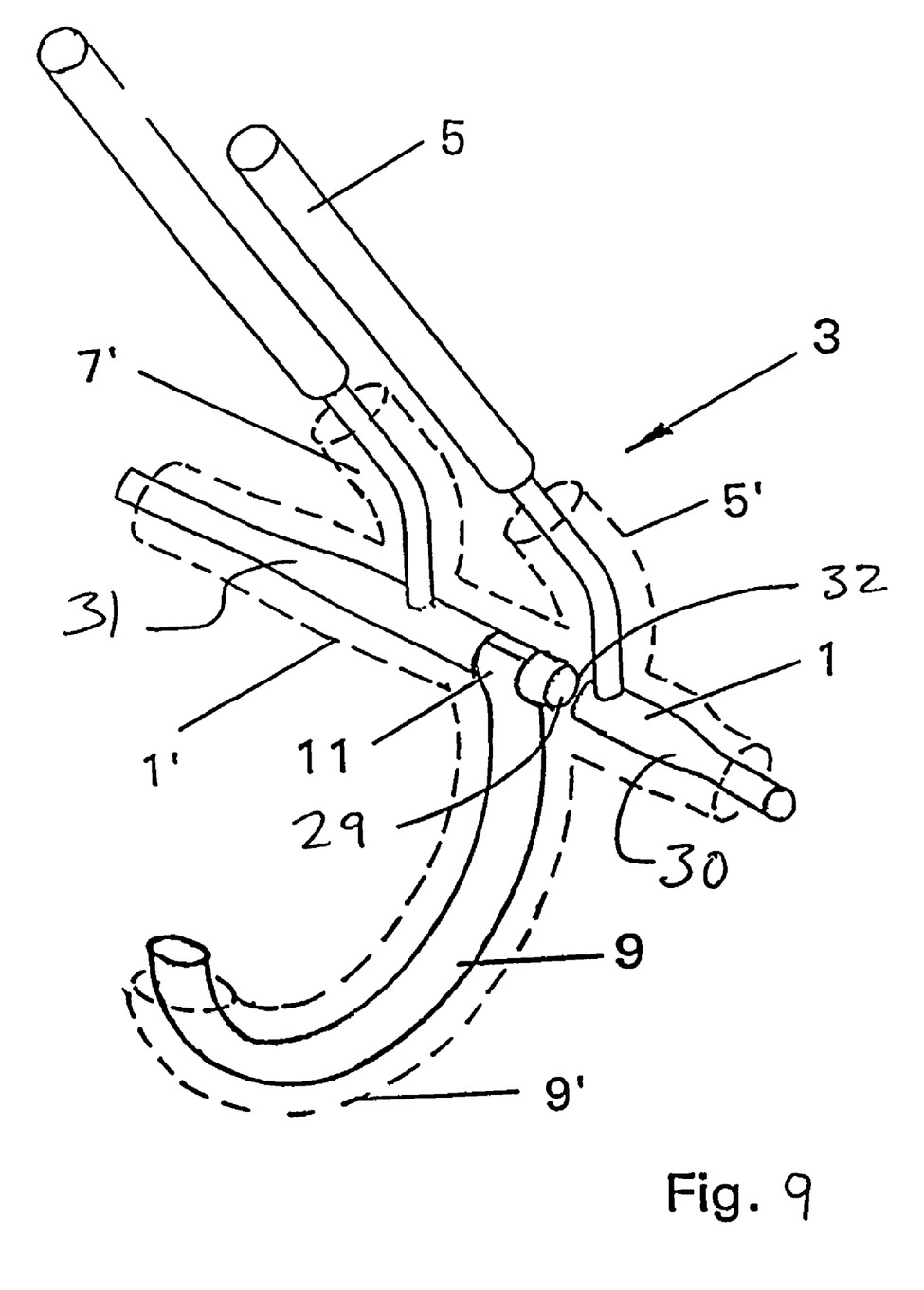
FIG. 9 is an orthogonal view of a cannula mandrel assembly for forming a septum or barrier in a void of the main body forming mandrel, with cannula forming polymeric material shown in ghost.

One modification of the present invention relates to the addition of a septum in the internal passage of the cannula to provide a barrier therein. The septum 29 divides the internal passage into two compartments or passageways so that a first one of the nares 5' can be coupled to an oxygen source (not shown) to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive, either continuously or intermittently during the sensed breathing cycle, a supply of oxygen.

To manufacture the septum 29, the main body forming mandrel 1 is formed as first and second separate, slightly spaced apart components 30, 31 which remain spaced apart from one another by a void 32 during the dipping operation of the manufacturing process so that the void 32 between the first and second separate, slightly spaced apart components 30, 31 is filled with the plastisol to form the septum 29. Once the cannula is cured, the septum 29 forms a barrier which divides the internal passage into two compartments or passageways.

Following sufficient curing, the nare mandrels 5 and 7 are removed from the blind holes 17 and 19 of main body mandrel 1 and the nares 5', 7' by pulling on enlarged diameter sections of nare mandrels 5 and 7, the mouthpiece mandrel 9 is removed from the mouthpiece 9' by disconnecting slot 27 of end connector 11 from rectangular section 21 of main body mandrel 1 and pulling the mouthpiece mandrel 9 through the mouthpiece 9'; and the first and second spaced apart components 30, 31 of the main body mandrel 1 are removed from the main body 1' of the cannula by pulling the first and second spaced apart components 30, 31 axially away from one another.

This variation of the manufacturing process is suitable for intermittent nocturnal oxygen delivery even though the patient breaths through his or her mouth.

Figure 10A:
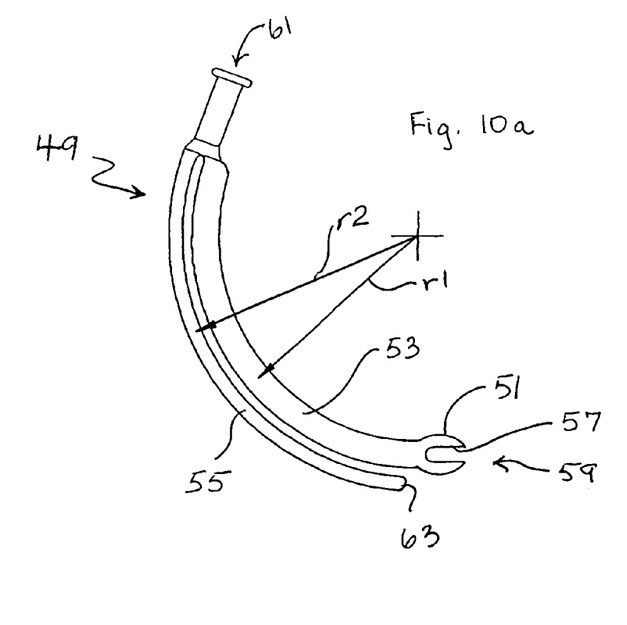
FIG. 10a-c are perspective, side bottom and rear view respectively of the mouthpiece mandrel detailing the fluid passage prong and the retainer prong.
Figure 10B:
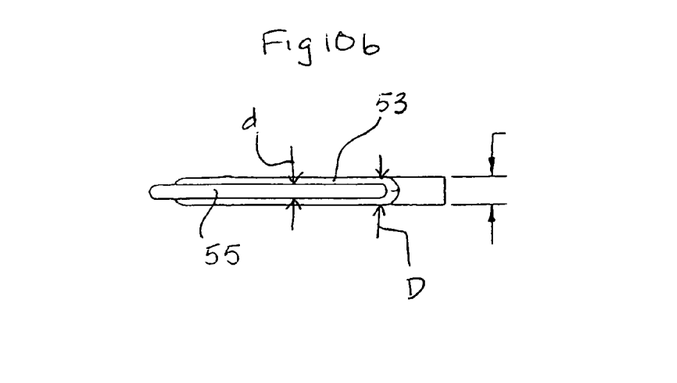
Figure 10C:
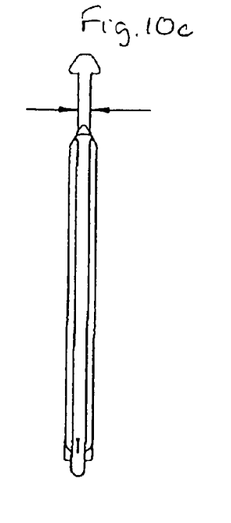

Another embodiment of the present invention provides the mandrel assembly with a divided mouthpiece mandrel 49 as shown in FIG. 10*a-c*. The mouthpiece mandrel is divided into a fluid passage prong 53 for forming a fluid passage in the mouthpiece of the finished cannula, and a retainer prong 55 for forming a retainer passage or cavity to receive a shape retaining material, or a dead soft material. The shape retaining material, or dead soft material permits the mouthpiece to be bent or molded into a desired shape or position and also retain such a desired shape or position. A further description of these features of the present embodiment follows below.

As in previous embodiments, in order to attach the mouthpiece mandrel 49 to the main body mandrel 1, the mouthpiece mandrel 49 includes an end connector 51 attached to a connecting end 59 of the fluid passage prong 53 of the mouthpiece mandrel 49. The end connector 51 has a slot 57 to slidably engage the rectangular section of the main body mandrel 1 as described with respect to the previous embodiments of the present invention. Slot 57 is sized to permit close contact of the slot 57 with the rectangular section 21 of main body mandrel 1 such that a snug fit is obtained to removably retain the mouthpiece mandrel 49 on the main body mandrel 1 while facilitating extraction from rectangular section 21 following partial curing and cooling of the PVC. As before, the outer surface of end connector 51 approximates the outer diameter of main body mandrel 1 to provide a uniform diameter of applied cannula material and to facilitate withdrawal of the mouthpiece mandrel 49 from the mouthpiece 69 of the cured cannula.

At a free end 61 of the mouthpiece mandrel 49 the respective ends of the fluid passage prong 53 and the retainer prong 55 are structurally joined so that the retainer prong is essentially supported by and attached to the fluid passage prong 53. The fluid passage prong 53 and the retainer prong 55 extend separately, and substantially parallel, along concentric radii of curvature r1, r2 between the free end at which they are joined, and the connecting end 59 of the mouthpiece mandrel 49. These radii of curvature are variable but are generally chosen to facilitate the functional alignment of the cannula mouthpiece with a patient's open mouth. These radii of curvature can be between about 0.5 inches to 2.5 inches and more preferably about 0.75 inches to 2.0 inches. The separation between the fluid passage prong 53 and the retainer prong 55 forms a gap which is a sufficient space between the extending structures so that during dipping operations which coat the mandrel with plastisol, no air pockets or voids are formed in the plastisol which flows into the gap between the fluid passage and retainer prong 55s.

As described above, the end connector 51 is attached to the fluid passage prong 53 at the connecting end 59 of the mouthpiece mandrel 49. The retainer prong 55 however merely terminates at a free end 63 adjacent the connecting end 59 of the mouthpiece mandrel 49. The free end 63 of the retainer prong 55 is spaced a sufficient distance from the end connector 51 and the connecting end 59 of the mouthpiece cannula 49 so as to eliminate the formation of air pockets or voids during dipping operations between the free end 63 of the retainer prong 55 and either or both the end connector 51 and the main body mandrel 1.

Observing FIG. 10b, the retainer prong 55 may be formed with an outer diameter d sized for forming a passage or cavity in the mouthpiece 69 for accepting and snugly encompassing a dead soft material for maintaining a change in the shape, form or curvature of the mouthpiece 69. By way of explanation, a dead soft material has substantially no structural memory of a previous shape or form which would cause the material to retain, or spring back to the previous shape or form. An example of a dead soft material to be used as a shape retaining support in the cannula formed by this embodiment is copper wire, either insulated or uninsulated although other dead soft materials for example, plastic are also contemplated. Copper is a highly malleable metal and generally retains whatever shape is imparted to it at a particular time without reverting or returning to a previous shape. Copper is also preferable in the present case over iron, steel or other ferromagnetic materials due to the propensity of nasal cannulas to be used on patients in certain electromagnetic and magnetic environments and diagnosis procedures.

An outer diameter D of the fluid passage prong 53 may be larger then the retainer prong diameter d due to fact that the fluid passage in the cannula must be sufficiently sized to provide an adequate fluid flow through the mouthpiece 49' of the cannula to supply a fluid or gas to a patient, for example via a demand regulator to a mouth breathing patient. Also the fluid passage formed by the fluid passage prong 53 must be of sufficient size to allow withdrawal, or sampling of a mouth breathing patient's exhalation gases.

Using the above described mouthpiece mandrel 49, all the above described parts of the entire mandrel assembly including the nare mandrels and the main body mandrel are assembled to define the interior spaces and passages of the cannula including the passage or cavity 79 for receiving the dead soft material. The cannula mandrel assembly is preheated to a desired temperature, and dipped in the cannula forming polymeric plastisol to provide a desired thickness of partially cured polymer on the cannula mandrel assembly to form the cannula. The cannula material is again heated placed in an oven to further cure the cannula material. Finally, the nare forming mandrels, the mouthpiece forming mandrel by removing the slot 57 from the rectangular recess, the mouthpiece mandrel including both the fluid passage prong 53 and the retainer prong 55, as well as the main body forming mandrel are extracted from the cannula material to leave the cured cannula 60 as shown in FIG. 11.

Figure 11:
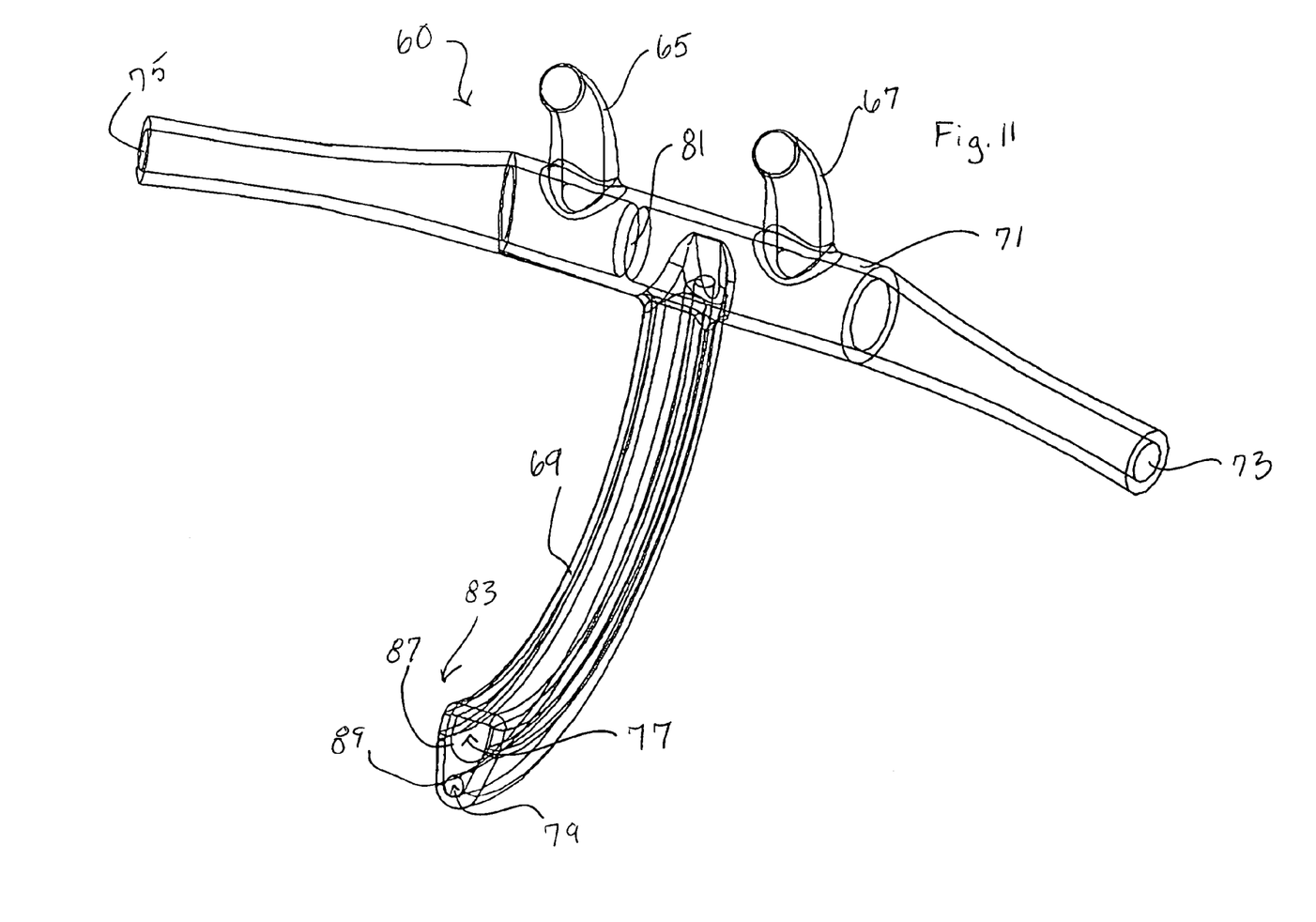
FIG. 11 is a perspective view of the cannula formed by the mandrel assembly and mouthpiece mandrel.

The nasal cannula as in FIG. 11, and as formed by the above described cannula mandrel assembly, has a pair of nasal prongs 65, 67 generally for insertion in the nares of a patient's nose, a main body 71 having opposing openings 73, 75 at either end of the main body 71 for coupling with gas delivery or gas sampling tubing, and positioned substantially in the middle of the main body 71 between the nasal prongs 65, 67 the mouthpiece 69 having the fluid passage 77 and the retainer passage or cavity 79 is connected to the main body.

Figure 12A:
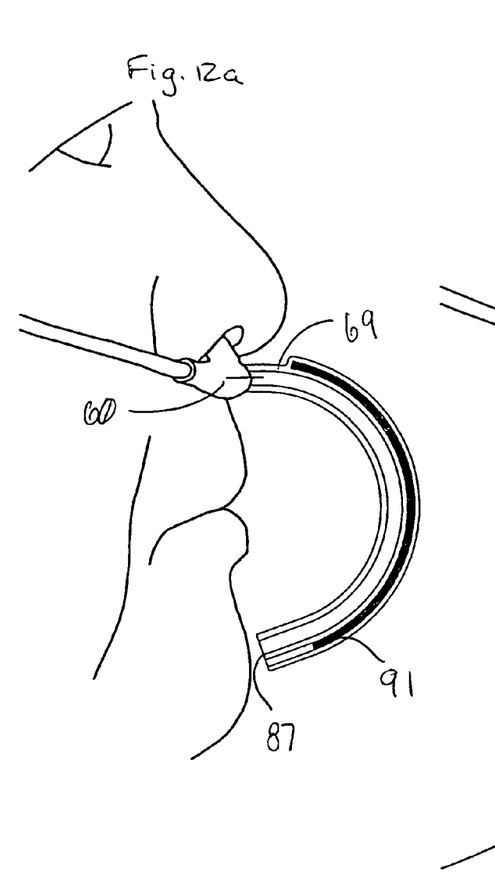
FIG. 12a-c are side views detailing the moldability and curvature change imparted to the mouthpiece to align the mouthpiece with the patient's oral inhalation/exhalation path.

As best seen in FIG. 12a the mouthpiece 69 of the nasal cannula 60 is formed with a neutral or original curvature corresponding to the curvature of the mouthpiece mandrel 49. As can be appreciated, due to the nature of the resiliency of the plastisol material which forms the cannula 60, in the absence of any dead soft material or external motivating force or support, the mouthpiece 69 will generally retain this original position, and if moved therefrom will also generally return or spring back to the original position once the motivation force is withdrawn.

Again observing FIG. 11, it is to be appreciated that the mouthpiece 69 is a unitary structure comprising the integrally formed passage 79 for receiving the dead soft material or the shape retaining material, as well as the fluid passage 77. The mouthpiece 69 is connected to and maintains a fluid communication with at least a portion of the main body 71 and at least one nasal prong 67, assuming an embodiment in which a septum 81 is formed, generally to divide the cannula 60 into either a gas sampling portion or an inhalation sensing portion. In any event, the connection between the main body 71 and the mouthpiece 69 includes the fluid communication between the interior of the main body 71 and the fluid passage 77 in the mouthpiece 69 as created by the fluid passage prong 53 of the mouthpiece mandrel.

Alternatively, it is to be appreciated that the mouthpiece 69 does not have to be centered between the nasal prongs 65, 67, not that the septum 81 be offset. It is conceivable that the mouthpiece could be offset from the center of main body 71. Furthermore, it is also conceivable that a second mouthpiece (not shown) which would permit gas delivery or sampling could be utilized could also be attached to the main body and thus a septum is such a case could be centrally located relative to the main body of the cannula. Also, as set forth in U.S. Pat. No. 6,439,234 to Curti et al. which is hereby incorporated by reference, additional openings could be provided in the nasal prongs as well as the mouthpiece to facilitate gas sampling and delivery.

The passage 79 for receiving the shape retaining material does not communicate with the interior of the main body 71. It is to be appreciated that due to the free end 63 of the retainer prong 55 of the mouthpiece mandrel being spaced from the connecting end 59 of the mouthpiece mandrel 49, a barrier is formed therebetween by the plastisol material during the dipping process so that there is no communication between the passage 79 for receiving the shape retaining material and the interior of the main body 71 of the cannula 60.

Now, considering the unconnected or free end 83 of the mouthpiece 69, both the fluid passage 77 and the passage 79 for receiving the shape retaining material terminate in respective and separate openings 87 and 89 which communicate with the surrounding environment. The fluid passage opening 87 provides the patient either with a gas, or withdraws a sample of exhalation gases from the patient. With respect to the passage 79, a suitable dead soft material as described above is introduced through the passage opening 89 and secured within the passage 79 to permit the moldability of the mouthpiece 69, i.e. the retention of a desired curve or shape, besides that of the original position, by the mouthpiece 69.

Figure 12B:
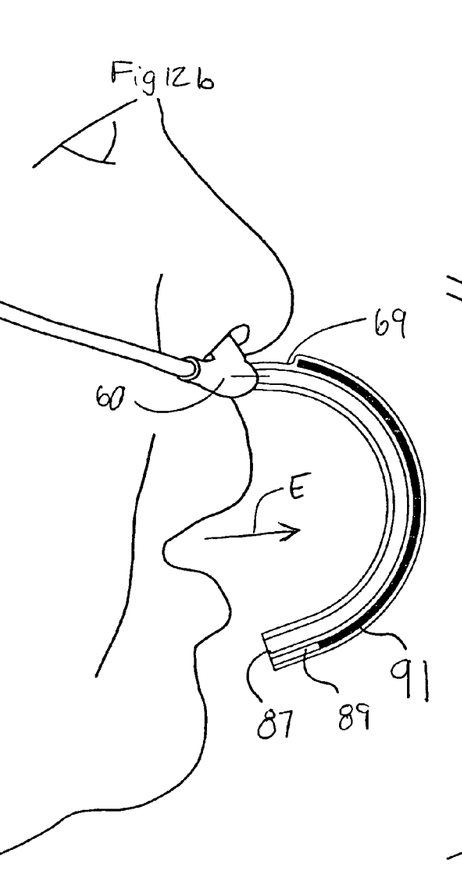
Figure 12C:
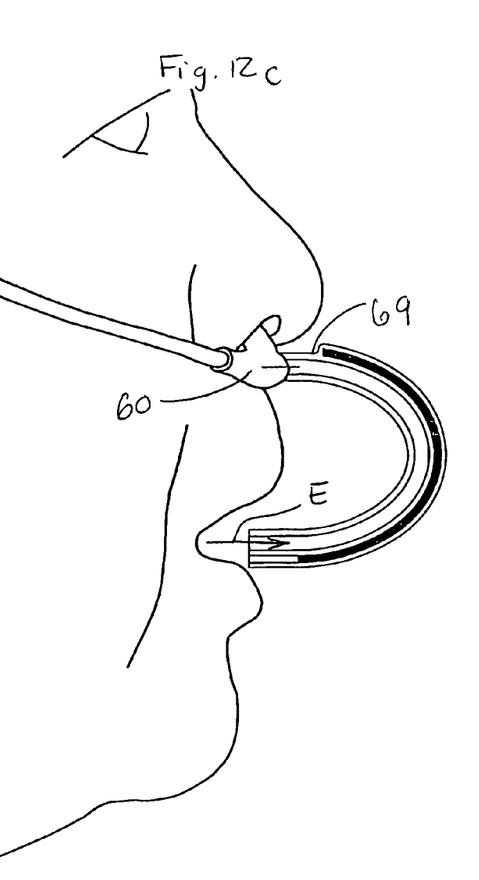

By way of example and now observing FIG. 12*a-c*, a shape retaining material or dead soft material, in this case a length of copper wire 91 approximately the same length as the passage 79 can be pushed or inserted into the passage 79 and secured therein by friction fit or more preferably by an adhesive which does not interfere with the bending of the mouthpiece 69. The wire 91 has a diameter and length which will fit within the diameter and length of the passage 79, i.e. the wire 91 is not exposed to the environment, and is long enough to provide appropriate shape retention to the flexible mouthpiece 69. The wire 91 can be coated with an adhesive and then inserted in the passage 79. The adhesive then cures to secure the wire 91 to the walls of the passage 79 and maintain the copper wire in the passage 79.

FIGS. 12*a* and 12*b* show the mouthpiece 69 and the wire 91 in the original position, with the patient's mouth closed and open respectively. As can be readily observed in FIG. 12*b*, the fluid passage opening 87 is not aligned with the patient's exhalation/inhalation path E. The moldability and shape retention characteristics of the wire 91 allow the mouthpiece 69 to be bent and appropriately maintained in a shape or form to align the fluid passage opening 87 with the exhalation/inhalation path E as shown in FIG. 12*c*. Such alignment and retention of the alignment permits both a more accurate delivery of gas in an inhalation and gas delivery use, as well as enabling a more accurate sampling of the patient's exhaled gases in the exhalation or sampling use. The above described structure thus permits the bending or molding of the mouthpiece 69 into a desired shape or form and ensures that such shape or form is maintained.

| Reference numerals | |
|---|---|
| 1 | main body mandrel |
| 1' | main body |
| 3 | cannula mandrel assembly |

-continued

| Reference numerals | |
|---|---|
| 5 | nare mandrel |
| 5' | nare mandrel |
| 7 | nare mandrel |
| 7' | nare |
| 9 | mouthpiece mandrel |
| 9' | mouthpiece |
| 11 | end connector |
| 13 | reduced diameter section |
| 15 | reduced diameter section |
| 17 | blind hole |
| 19 | blind hole |
| 21 | rectangular recessed section |
| 23 | enlarged diameter section |
| 25 | enlarged diameter section |
| 27 | slot |
| R | radius |
| T | rectangular section shoulder depth |
| W | rectangular section width |
| X | mouthpiece mandrel radius |
| Y | main body diameter |
| Z | rectangular section thickness |

We claim:

1. A method of forming a cannula comprising the steps of:
   assembling a cannula mandrel assembly comprising separable engageable parts including a main body mandrel, at least one nasal prong mandrel, and a mouthpiece mandrel including a fluid passage prong having a first end to connect with the main body mandrel and a retainer prong spaced apart from and extending along the fluid passage prong and having a first end terminating adjacent the main body mandrel;
   heating the cannula mandrel assembly to a desired temperature;
   providing an uncured cannula forming polymeric material in flowable state;
   applying at least one coating of the polymeric material to the cannula mandrel assembly to provide a desired material thickness coating on the cannula mandrel assembly and forming the cannula;
   at least partially curing the coating of the polymeric material on the cannula mandrel assembly; and
   disassembling the cannula mandrel assembly by withdrawing the at least one prong mandrel, the mouthpiece mandrel including the fluid passage prong and the retainer prong and the main body mandrel from the formed cannula, and
   introducing a shape retaining material into a retainer passage formed by the retainer prong.

2. The method according to claim 1, further comprising the step of supporting the at least one nasal prong mandrel by a nasal prong attachment portion of the main body mandrel, and supporting the mouthpiece mandrel by a mouthpiece attachment portion of the main body mandrel.

3. The method according to claim 2, further comprising the step of forming the nasal prong attachment portion in the main body mandrel and the mouthpiece attachment portion in the main body mandrel as one of a hole and a recess sized for slidably mating with an attachment end of the nasal prong mandrel and an attachment end of the mouthpiece mandrel.

4. The method according to claim 2, further comprising the step of slidably engaging an attachment end of the mouthpiece mandrel with the main body mandrel.

5. The method according to claim 4, further comprising the step of assembling the mouthpiece mandrel with the main body mandrel such that the mouthpiece mandrel extends radially from and substantially perpendicular to the main body mandrel.

6. The method according to claim 4, further comprising the step of assembling the mouthpiece mandrel with the main body mandrel such that the mouthpiece mandrel extends radially from and substantially perpendicular to the main body mandrel with a planar surface of the main body mandrel abutting against a mating planar surface of the mouthpiece mandrel.

7. The method according to claim 5, further comprising the step of manufacturing the cannula mandrel assembly from beryllium copper.

8. The method according to claim 1, further comprising the step of manufacturing the cannula mandrel assembly from beryllium copper.

9. The method according to claim 1, further comprising the step of applying the polymeric material to the cannula mandrel assembly by a dipping process.

10. The method according to claim 1, further comprising the step of heating the cannula mandrel assembly at a temperature of from about 350° F. to about 550° F. prior applying the polymeric material to the cannula mandrel assembly.

11. The method according to claim 1, further comprising the step coating the cannula mandrel assembly with a layer of release material prior to applying at least one coating of the polymeric material thereto.

12. The method according to claim 1, further comprising the step of applying a plurality of coatings of the polymeric material to the cannula mandrel assembly by a plurality of dipping steps.

13. The method according to claim 1, further comprising the step of partially curing the polymeric material by heating the polymeric material at a temperature of from about 410° F. to about 450° F.

14. A method of forming a cannula having at least a mouthpiece lumen for one of sampling an expired gas and supplying a desired gas, the method comprising the steps of:
   a) assembling a cannula mandrel assembly, from a plurality of separate parts comprising first and second nasal prong forming mandrels, a main body forming mandrel and at least one mouthpiece forming mandrel including a fluid passage prong having a first end to connect with the main body mandrel and a retainer prong spaced apart from and extending along the fluid passage prong and having a first end terminating adjacent the main body mandrel, by removably coupling a respective end connection of each of the first and the second nasal prong forming mandrels to the main body forming mandrel, and removably coupling an end connection of the fluid passage prong of the mouthpiece forming mandrel to the main body forming mandrel;
   b) heating the cannula mandrel assembly to a desired temperature;
   c) applying a desired thickness of a plastisol of a polymeric material to the heated cannula mandrel assembly;
   d) at least partially curing the applied polymeric material;
   e) extracting the first and second nasal prong forming mandrels, the mouthpiece forming mandrel, and the main body forming mandrel from the at least partially cured polymeric material to form the cannula having at least a mouthpiece lumen for one of sampling an expired gas and supplying a desired gas, and
   f) introducing a shape retaining material into a retainer passage formed by the retainer prong.

15. The method according to claim 14, further comprising the step of removably coupling the end connection of the mouthpiece forming mandrel to a central region on one side of the main body forming mandrel, removably coupling the end connection of the first nasal prong forming mandrel to an opposite side of the main body forming mandrel spaced apart from the mouthpiece forming mandrel, and removably coupling the end connection of the second nasal prong forming mandrel to the opposite side of the main body forming mandrel spaced apart from the mouthpiece forming mandrel such that the mouthpiece forming mandrel is located between the first and second prong forming mandrels.

16. The method according to claim 14, further comprising the step of partially curing the polymeric material using heat from the heated cannula mandrel assembly and further curing of the polymeric material in an oven.

17. The method according to claim 14, further comprising the step of applying the polymeric material by a dipping process.

18. The method according to claim 14, further comprising the step of forming one of a hole and a recess in the main body forming mandrel to facilitate removably coupling the respective end connection of each of the first and the second prong forming mandrels and the mouthpiece forming mandrel to the main body forming mandrel.

19. The method according to claim 18, further comprising the step of removably coupling the mouthpiece forming mandrel with the main body mandrel such that the mouthpiece mandrel extends radially from and substantially perpendicular to the main body mandrel with a planar surface of the main body mandrel abutting against a mating planar surface of the mouthpiece mandrel.

20. A method of forming a cannula with a pair of nasal prongs and a mouthpiece lumen communicating with a main body of the cannula, the method comprising the steps of:
   constructing a cannula mandrel assembly by attaching first and second nasal prong forming mandrels to corresponding first and second main body forming mandrel components and attaching a mouthpiece forming mandrel to at least one of the first and second main body forming mandrel components, the first and the second main body forming mandrel components being spaced apart to form first and second main body passages separated by a septum and the mouthpiece forming mandrel including a fluid passage prong having a first end to connect with the at least one of the first and second main body mandrel components and a retainer prong spaced apart from and extending along the fluid passage prong and having a first end terminating adjacent the at least one of the first and the second main body forming mandrel components;
   heating the cannula mandrel assembly to a desired temperature;
   providing a cannula forming polymeric material as a plastisol;
   applying a desired thickness of the plastisol to the heated cannula mandrel assembly;
   curing the plastisol by application of heat;
   disengaging the pair of nasal prong forming mandrels and the mouthpiece forming mandrel from the main body forming mandrel and extracting the main body forming mandrel from the cured plastisol to form the cannula having a pair of nasal prongs and a mouthpiece lumen communicating with a main body of the formed cannula for one of sampling an expired gas an desired gas, and
   introducing a shape retaining material into a retainer passage formed by the retainer prong.

* * * * *